(12) United States Patent
Alabdulkareem

(10) Patent No.: US 11,819,632 B2
(45) Date of Patent: Nov. 21, 2023

(54) ENDOVASCULAR CATHETER WITH CONTROLLABLE TIP

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Mohammed Adnan Alabdulkareem, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 947 days.

(21) Appl. No.: 16/795,150

(22) Filed: Feb. 19, 2020

(65) Prior Publication Data

US 2021/0252253 A1    Aug. 19, 2021

(51) Int. Cl.
| | | |
|---|---|---|
| A61M 25/01 | (2006.01) | |
| A61M 25/09 | (2006.01) | |
| A61M 25/00 | (2006.01) | |
| A61L 29/08 | (2006.01) | |
| A61L 29/16 | (2006.01) | |
| A61L 29/14 | (2006.01) | |

(52) U.S. Cl.
CPC ....... *A61M 25/0105* (2013.01); *A61L 29/085* (2013.01); *A61L 29/141* (2013.01); *A61L 29/16* (2013.01); *A61M 25/0012* (2013.01); *A61M 25/0045* (2013.01); *A61M 25/09* (2013.01); *A61M 2025/09058* (2013.01); *A61M 2025/09133* (2013.01)

(58) Field of Classification Search
CPC .......... A61M 25/0012; A61M 25/0105; A61M 25/0045; A61M 25/0147; A61M 25/005; A61M 25/0144
See application file for complete search history.

(56) References Cited

U.S. PATENT DOCUMENTS

| | | |
|---|---|---|
| 2004/0138525 A1 | 7/2004 | Saadat et al. |
| 2016/0287223 A1 | 10/2016 | Hongston et al. |
| 2019/0192820 A1 | 6/2019 | Olson et al. |

FOREIGN PATENT DOCUMENTS

EP    2 550 989 B1    6/2019

OTHER PUBLICATIONS

Takizawa, et al. ; Development of a Microfine Active Bending Catheter Equipped With MIF Tactile Sensors ; Olympus Optical Co., Ltd. ; Aug. 6, 2002 ; 7 Pages.

*Primary Examiner* — Tiffany Legette
(74) *Attorney, Agent, or Firm* — Oblon, McClelland, Maier & Neustadt, L.L.P.

(57) ABSTRACT

A steerable endovascular catheter which can be used and for diagnosis and endovascular treatment of vascular diseases. Methods of diagnosis and endovascular treatment comprising steering the catheter through vasculature of a patient.

20 Claims, 14 Drawing Sheets

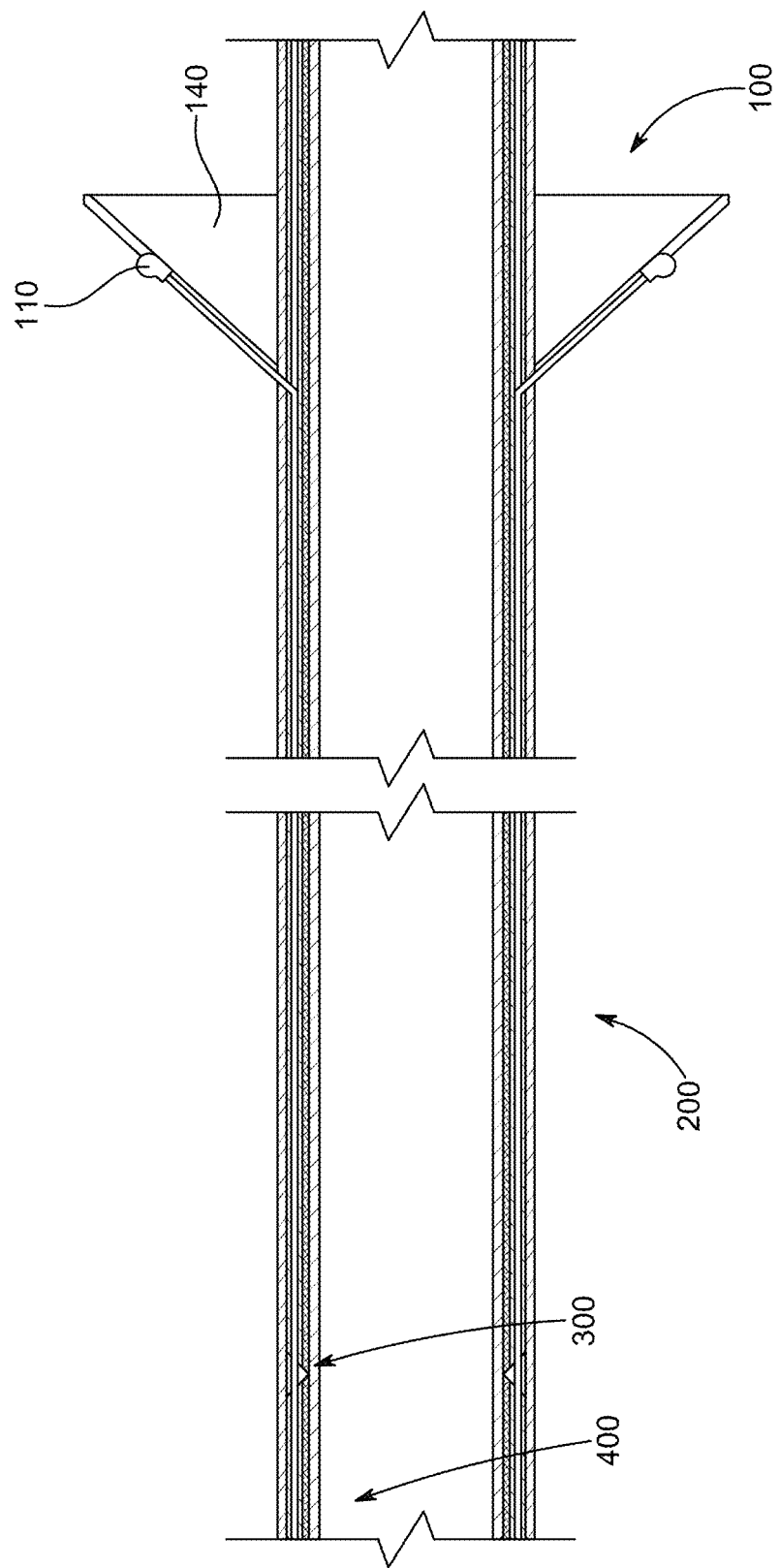

ENDOVASCULAR CATHETER WITH CONTROLLABLE TIP

BACKGROUND OF THE INVENTION

Field of the Invention

The invention pertains to the field of medicine including cardiology, radiology and neuroradiology and more specifically to a steerable endovascular catheter used for diagnosis and endovascular treatment of vascular diseases.

Description of Related Art

Endovascular therapy—the treatment of cardiovascular disease from inside the blood vessel—has changed the way heart attacks, stroke and other cardiovascular conditions are treated. Many heart and vascular problems that once required invasive surgery can now be treated from inside the body using less invasive endovascular procedures. Examples of endovascular therapy include endovascular access to niduses which form parts of vascular malformations via the tortious vasculature in the brain as depicted by FIGS. 1A-1C. FIG. 1A depicts a normal digital angiogram of the brain showing its tortious vasculature. Endovascular treatment is generally less painful and traumatic that conventional surgical methods and reduces the amount of time a patient spends in the hospital and in recovery.

Specialized catheters and equipment have been designed to facilitate minimally invasive endovascular catheter-based procedures. These include the specialized catheters described in FIGS. 2A-2C which are typically threaded through the vascular system using a guidewire. Guidewires are commonly used in the field of medicine. They are used to navigate the torturous pathways of anatomy. Guide wires can be inserted through an orifice of a body, or surgically inserted. The wire is pushed, turned, or otherwise manipulated at a proximal end which remains outside the body. An operator can pull, push or turn/circle the guidewire around its center to facilitate targeting a site of interest. The forces applied to the proximal end translate down the wire to a distal end. The distal end can provide various procedure specific functions inside the body. A guidewire can be made from various materials, with metal being common. Guidewires also come in a wide range of diameters, commonly about 0.015 to about 0.05 inches in diameter, such as 0.035 or 0.038 inches in diameter. Guidewire coatings and finishes can provide benefits for a given procedure. A common application for a guidewire is with an endovascular procedure. A guidewire may be placed inside the lumen of the catheter and withdrawn when the target site is reached, thus permitting the catheter to assume its predetermined shape. However, this guidewire can kink inside the catheter due to its small size and due to pressure applied to it making handling problematic or even directing the catheter into the wrong vessel. Moreover, the operator lacks precise control of the catheter and cannot easily guide it to the desired target site or vessel.

There is a need for an endovascular catheter with a steerable tip as commercially available catheters either have a straight or various types of curved tips as shown by FIGS. 2A-2C.

Most operators use a guidewire with a catheter to help them guide the catheter. However, some of an expert physician may use a conventional catheter without a guidewire in straightforward and easy cases or in a patient having less complex or tortuous anatomy.

Endovascular procedures are often performed in a cardiac catheterization lab and typically require only a small incision through which a thin catheter is inserted. Using advanced imaging technology, the catheter is guided using a guidewire through a blood vessel to remove blockages and/or open narrowed areas, such as blocked coronary arteries. These non-surgical procedures are also known as percutaneous coronary interventions (PCI) and include catheterization for balloon angioplasty or percutaneous transluminal coronary angioplasty (PTCA), which is one of the most common procedures for opening obstructed coronary arteries; angioplasty with stent placement; drug-eluting stent placement; renal artery angioplasty and stenting; carotid artery stenting; transfemoral carotid artery stenting; and transcarotid artery revascularization.

Limitations of conventional endocatherization include difficulty in controlling and guiding the catheter through the vascular system and in the high amount of procedure time that is consumed trying to reach the target lesion or vessels while passing inside multiple tortuous vessels.

In view of the limitations of existing medical devices and procedures, the inventor sought to design a endovascular catheter that allows the operator to easily and accurately control navigation of the catheter tip through tortuous vessels of the vascular system so that the target lesion or site may be reached safely and quickly.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

The catheter device as disclosed herein allows the operator to control the catheter tip, so that it can be easily and safely navigated through tortuous vessels of vascular system and more quickly reach a target lesion or endovascular location. Unlike conventional endovascular catheters the invention contains a circumferential V-shaped void or "defect" at its distal end that permit the defect to act as a joint. Preferably, the catheter as disclosed herein is used for endovascular procedures; however, the present invention is applicable to any medical procedure utilizing a catheter.

This joint can be manipulated using multiple guidewires that pass along the tubular section of the catheter and through this V-shaped void or defect to the distal end of the catheter. These multiple guidewires are manipulated using control shell at the exterior proximal end of the device to steer the catheter tip through the vasculature by bending the distal tip via this joint.

The steerable catheter as disclosed herein may employed in a variety of different endovascular diagnostic and therapeutic procedures including for intervention neuroradiology, intervention radiology and intervention cardiology.

Compared to existing devices, the catheter of the invention reduces the procedure time and operator fatigue, increases productivity of medical personnel as more procedures can be done within the same amount of time, causes less trauma to vessels, and reduces the risk of complications during a medical procedure such as thrombosis or infection, and increases the accuracy of targeting complex vascular lesions including aneurysms and arteriovenous vascular malformations.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 4B depicts a lateral cross-section of the catheter device including handle section 100 housing guidewire tips 110 and control shell 140, tubular catheter section 200, circumferential joint or "defect" 300, and steerable distal tip 400.

DETAILED DESCRIPTION OF THE INVENTION

Figure 1A:
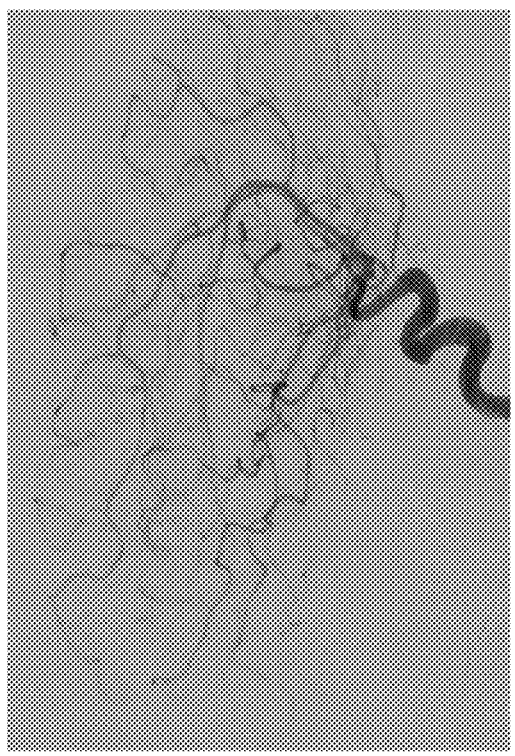
FIG. 1A is an angiogram of the normal vasculature of the brain.
Figure 1C:
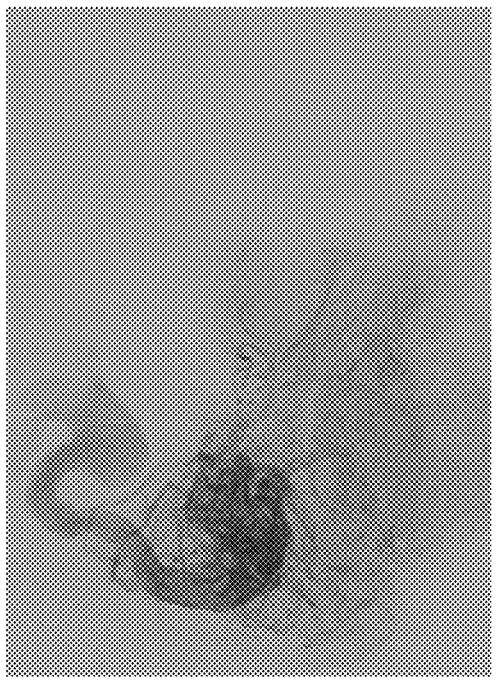
FIGS. 1B and 1C depict a nidus or abnormal tangle of small vessels in the vasculature of the brain such as an arteriovenous malformation (AVM).
Figure 1B:
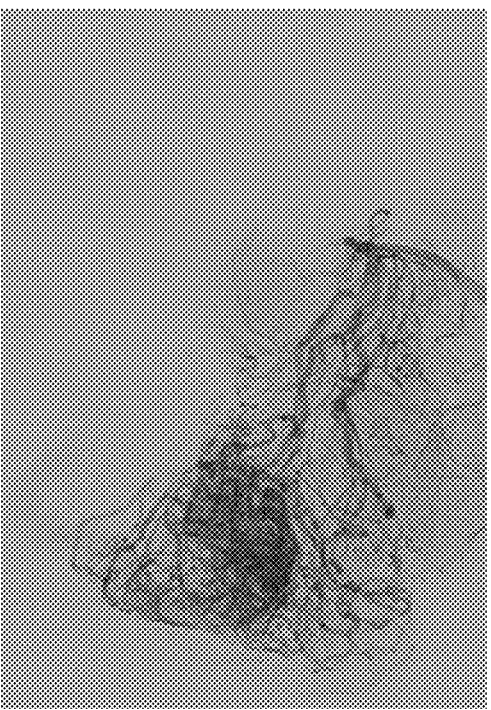
Figure 2A:
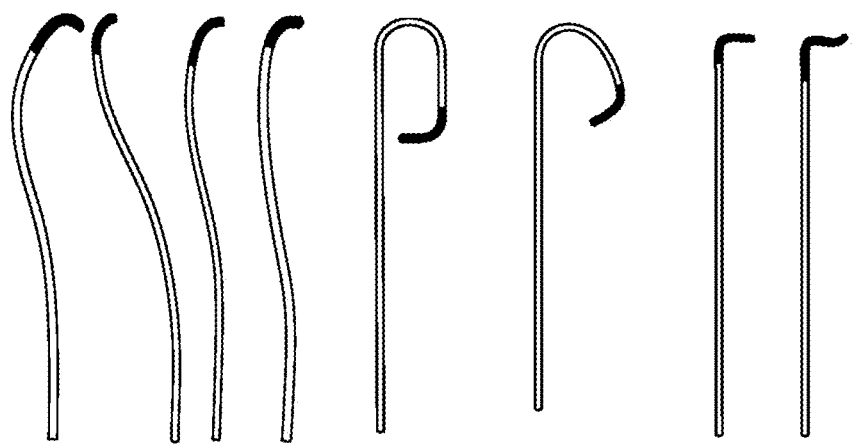
FIGS. 2A-2C depict a variety of different specialized catheters having different shapes and gauges.
Figure 2B:
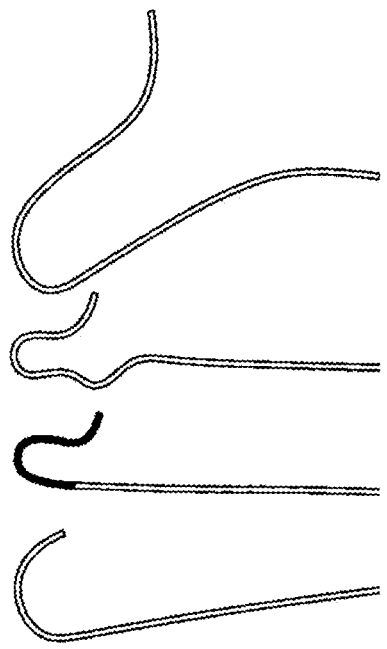
Figure 2C:
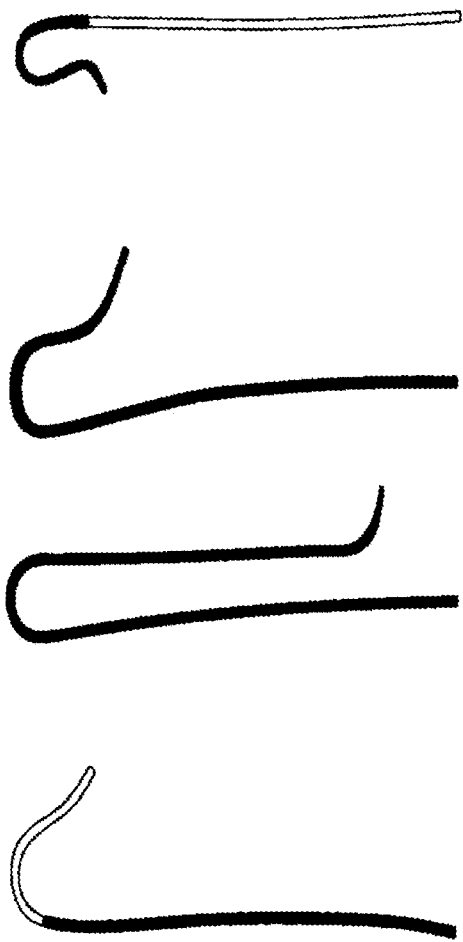
Figure 2D:
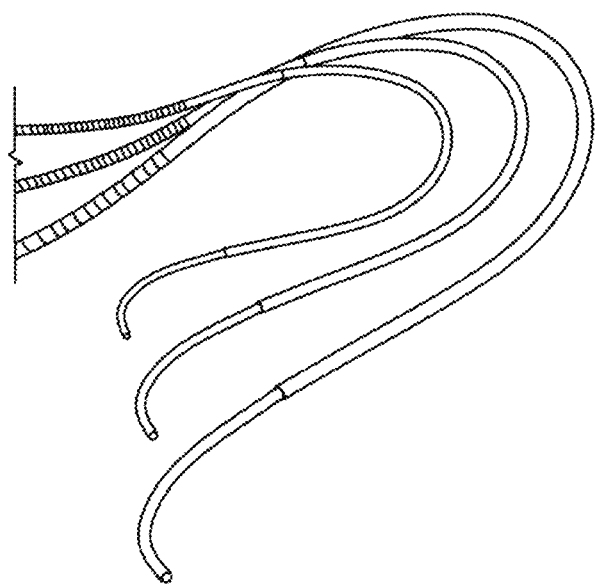
FIGS. 2D and 2E depict guidewire packages.
Figure 2E:
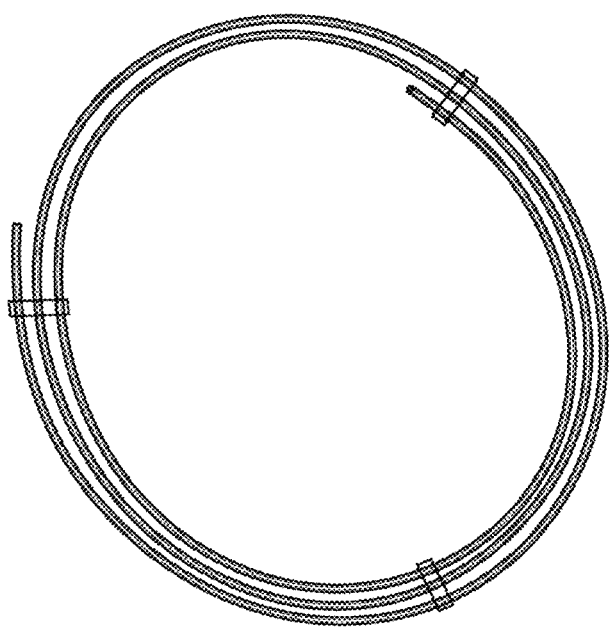
Figure 3A:
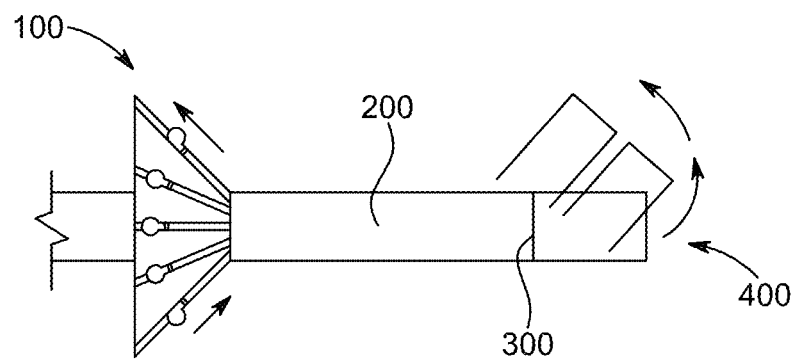
FIGS. 3A and 3B depict two views of one embodiment of the steerable catheter of the invention which includes the handle section 100, tubular catheter section 200, joint 300, and steerable distal end 400. As shown by the arrows adjacent to the handle portion 100, the distal tip 400 may be steered by pulling or manipulating the wire threads or guidewires, which longitudinally extend through tubular catheter section 200, via the handle containing the control shield as depicted in more detail by FIGS. 4A-4B.
Figure 3B:
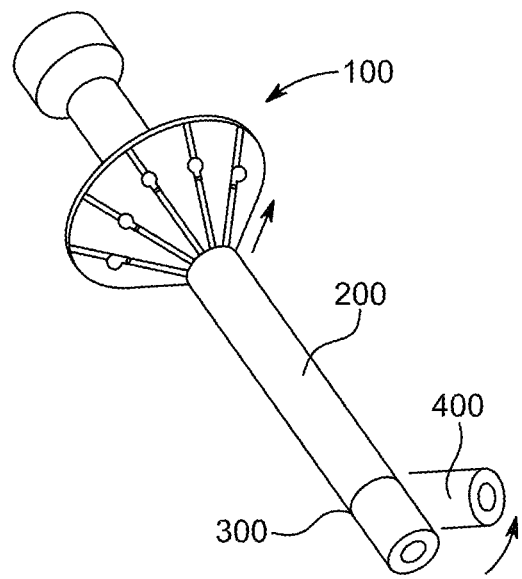
Figure 4A:
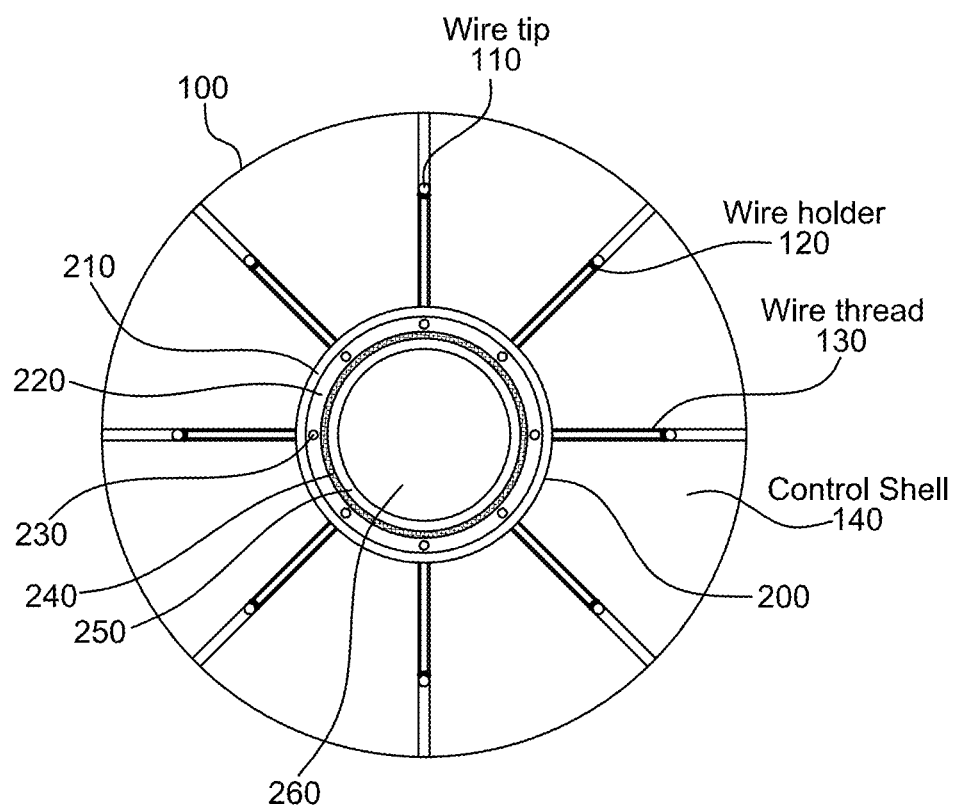
FIG. 4A depicts an axial view of the handle section 100 and tubular catheter section 200 of an embodiment of the invention. The handle section includes wire tip 110 which at the proximal end of the guidewires in tubular section 200, wire holder 120, guidewire thread 130 which extends to the distal end of tubular section 200, and control shell 140. The tubular section 200 includes outer layer 210, intermediate layer 220, guidewire 230 embedded in the intermediate layer 220, support or mesh-like layer 240, inner layer 250 which is directly adjacent to lumen 260.
Figure 5A:
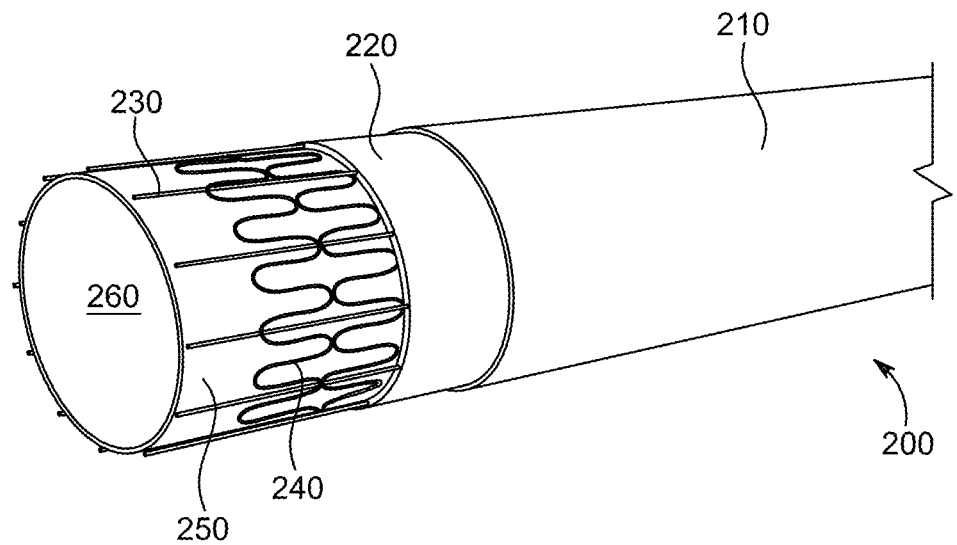
FIG. 5A shows the layered structure of tubular catheter section 200 including outer layer 210, intermediate layer 220, longitudinal guidewires 230, support or mesh-like layer 240, inner layer 250 and lumen 260.
Figure 5B:
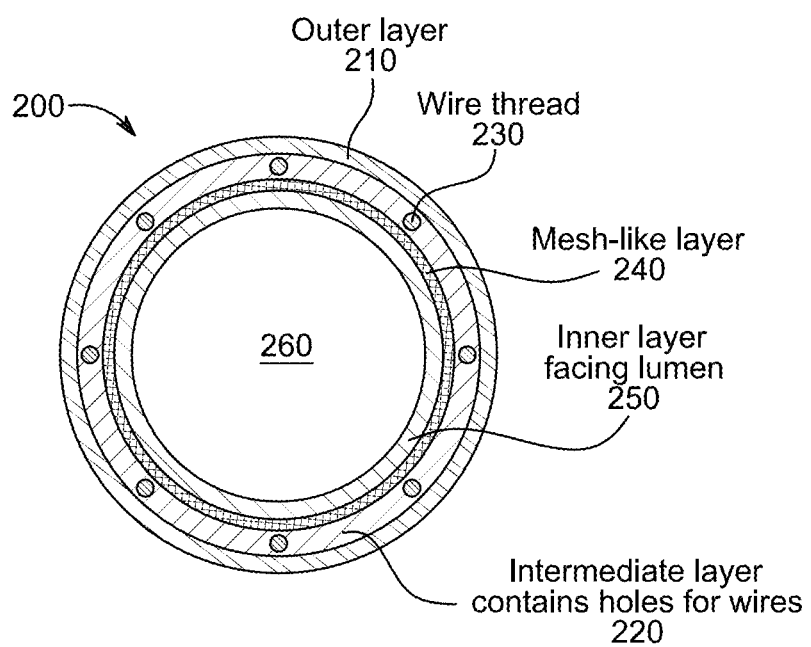
FIG. 5B provides an axial cross-sectional view of tubular catheter portion 200 which includes outer layer 210, intermediate layer 220 which embeds wire threads 230, support or mesh-like layer 240, an inner layer 250 which directly faces the lumen.
Figure 6A:
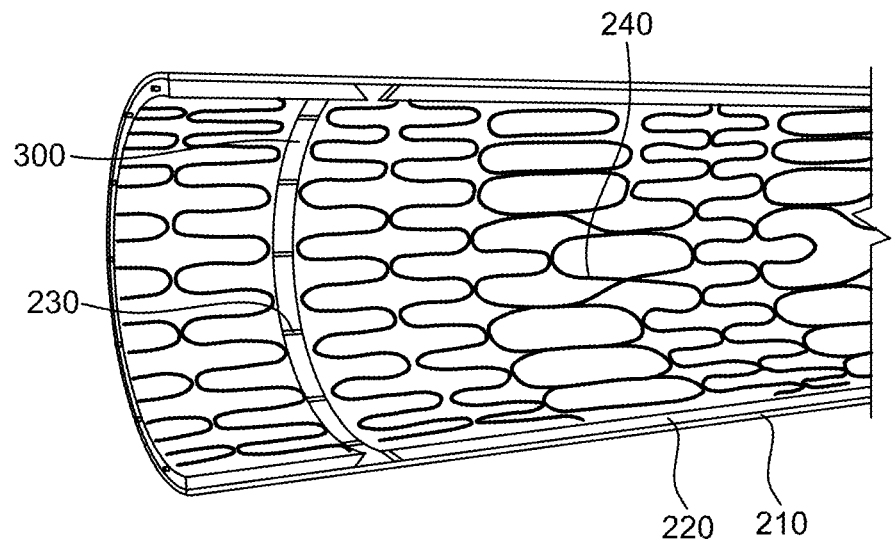
FIGS. 6A and 6B detail the circumferential joint or "defect" which interrupts intermediate layer 220 and support or mesh-like layer 240. Wire threads or guidewires 230 continue uninterrupted through this joint or defect layer. The joint or defect has a substantially triangular cross section 310 with the apex of the triangle facing inward. As shown by both figures external layer 210 is not interrupted by the joint, void, or defect 300.
Figure 6B:
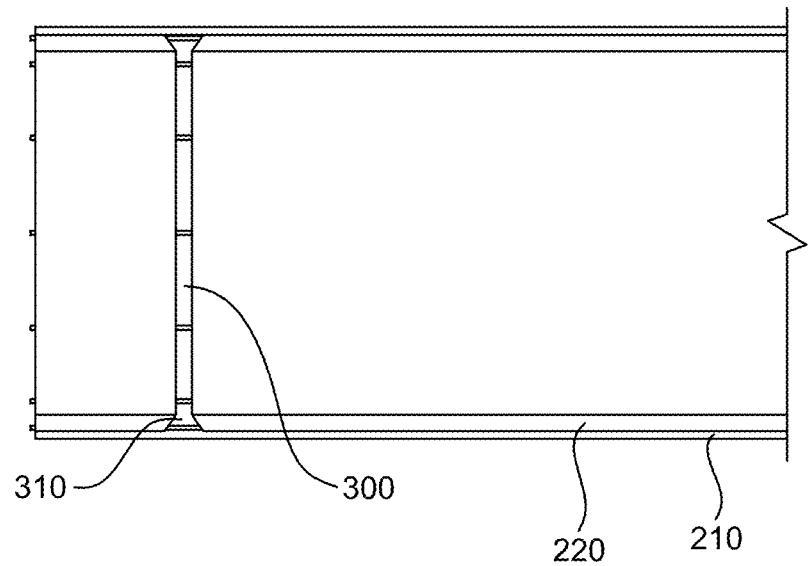
Figure 6C:
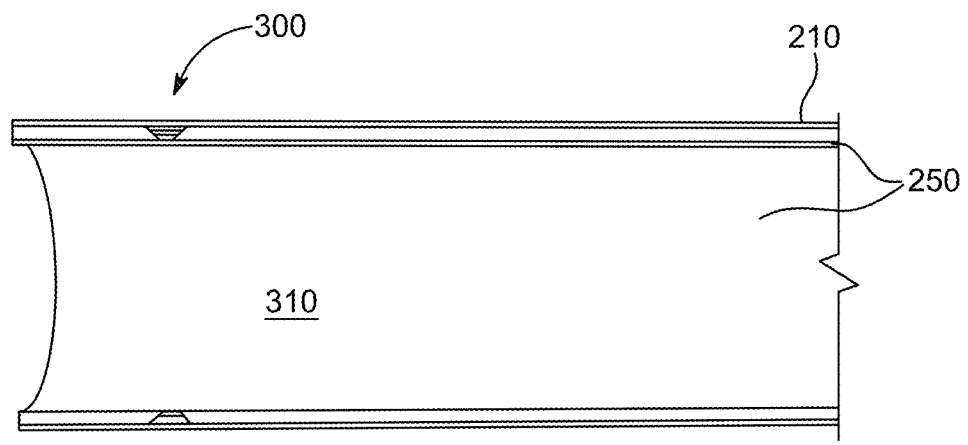
FIGS. 6C and 6D depict the circumferential joint or "defect" 300 and shows that it does not interrupt external layer 210 or internal layer 250.
Figure 6D:
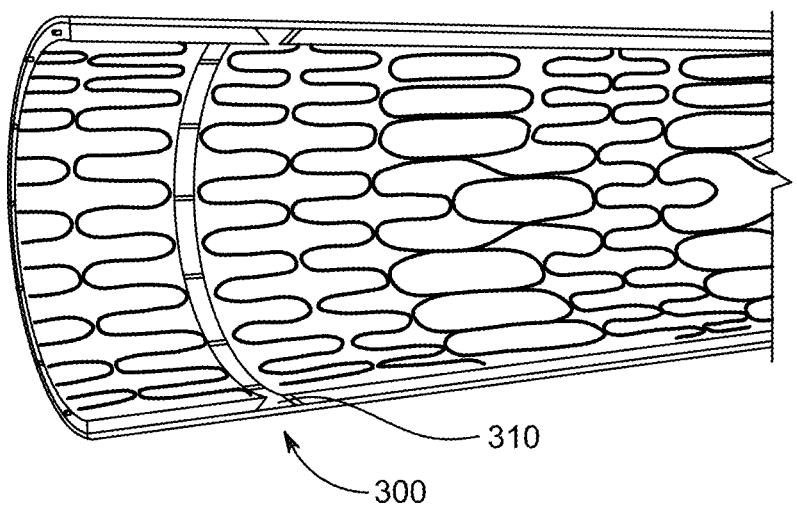
Figure 6E:
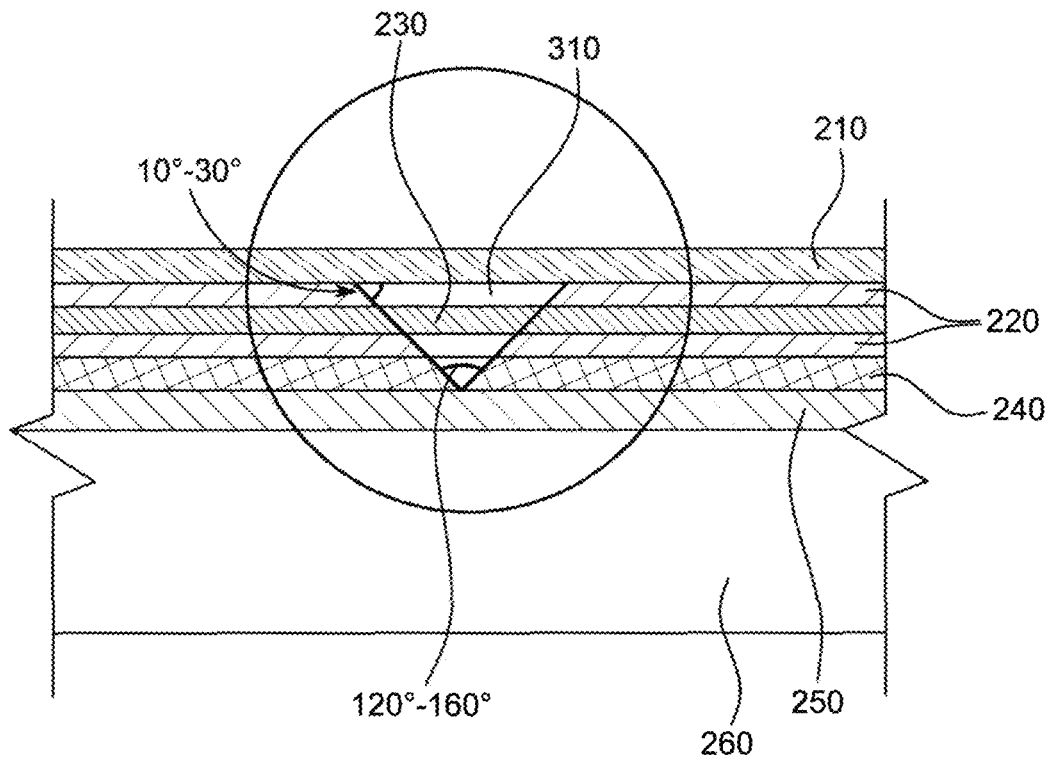
FIG. 6E describes the cross-section of the circumferential joint or defect 300 in greater detail. As shown, the circumferential gap has a substantially triangular cross-section 310 that interrupts the intermediate 220 and support or mesh-like tubular layers 240, but which does not extend through the inner layer and is not open to the lumen 260. The wire threads 230 pass through this defect which interrupts intermediate layer 220 and mesh-like layer 240.

The invention as disclosed herein includes, but is not limited to, the following embodiments.

One embodiment of the invention is directed to a steerable catheter, preferably sized and configured for use as an endovascular catheter, comprising, consisting essentially of, or consisting of an external control shell and, in order from external to internal, the following tubular layers and lumen: an outer layer, an intermediate layer, a support layer, and an inner layer that faces a lumen; wherein the intermediate layer embeds two to ten longitudinal guidewires spanning the length of the catheter which are longitudinally threaded through the intermediate layer and attached at their distal ends to the distal end of the catheter and attached at their proximal ends to the external control shell, and wherein the intermediate layer and the support layer comprises a circumferential V-shaped void, space, or "defect" which acts as a joint. The location of the V-shaped void is selected depending on the type of procedure and endovascular course to be followed during a particular procedure. In most embodiments, the V-shaped void is about 1 to 5 cm from the distal end or tip of the catheter. The void usually has a V-shaped cross-section with the apex of the V facing inward and the void dividing the intermediate and support layers into unconnected distal and proximal intermediate and support layers. However, the void does not divide the outer and inner layers, which act as coverings or respectively as an outer skin exposed to the vasculature and inner skin lining the open or hollow lumen of the device and does not interrupt the longitudinal guidewires longitudinally movably inlayed, threaded, or embedded in the intermediate layer, which longitudinally extend from the proximal end of the device containing an external handle or control shell to the distal tip of the catheter. These guidewires occupy and are able to move within longitudinal cavities in the intermediate layer. In some embodiments, the intermediate layer contains an annular space between the guidewire and the portions of the intermediate layer surrounding the wires. In some embodiments, this space may comprise a lubricant, or in other embodiments the guidewires or longitudinal cavities of the intermediate layer surrounding the guidewires may be lined with a lubricating material such as PTFE, to facilitate longitudinal movement of the wires.

Usually, the inner layer is made from a low-friction or frictionless material such as PTFE and directly surrounds the lumen or hollow space inside the tubular section of the catheter, but in some embodiments, may further comprise an additional low-friction or frictionless coating or lubricant.

In one embodiment, the endovascular catheter of the invention comprises eight guidewires within the intermediate layer of the catheter wall extending uninterrupted from the distal tip of the catheter to the control shell. Their distal ends are attached to the tip of the catheter distal to the joint created by the void or defect. However, the intermediate layer containing the wires is contained within or covered by the external layer and an internal layer adjacent to the lumen of the catheter. The proximal ends of the guidewires extend outside of the body into an external control shell which permits each wire to be pulled, pushed or manipulated so as to steer the tip of the catheter through the vasculature.

When an operator of the catheter uses the control shell to pull a guidewire contained in the tubular section of the catheter, the tip of the catheter on the distal end of the joint, void or defect, is moved in a particular direction. By using the control shell to pull the ends of different guidewires the tip of the catheter can be directed left, right, up or down (or combinations of these directions) through the vasculature as needed.

Figure 10:
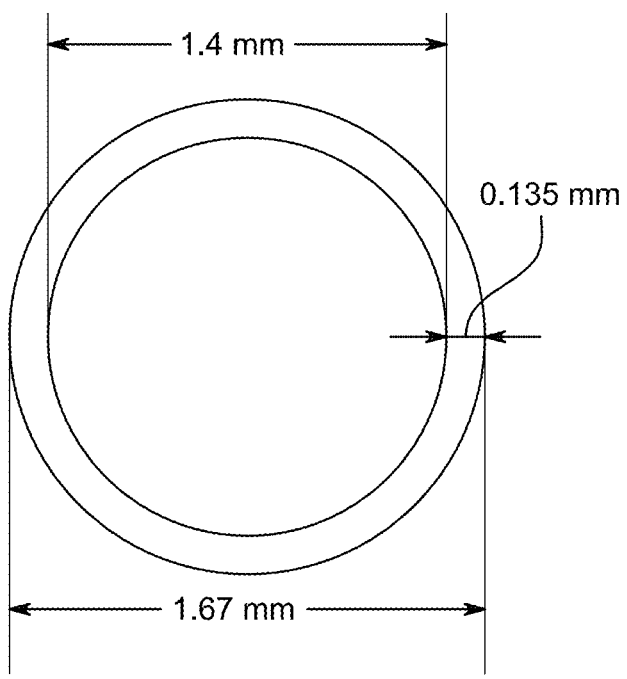
FIG. 10 depicts an embodiment of the catheter having an outer diameter of 5 French or 1.67 mm, a wall thickness of 0.135 mm, and an inner diameter of 1.4 mm.

The thickness of the outer layer of the catheter can range from about 0.02, 0.03, 0.04, 0.05, 0.06, 0.07 to 0.08 mm, the thickness of the intermediate layer can range from about 0.02, 0.03, 0.04, 0.05 to 0.06 mm, the thickness of the support layer can range from about 0.012, 0.013, 0.014, 0.015, 0.016, 0.017, 0.018, 0.019 to 0.020 mm; and the thickness of the inner layer can range from 0.015, 0.020, 0.025, 0.030, 0.035, 0.040 to 0.045 mm; wherein the total thickness of the tubular layers excluding the lumen does not exceed 0.100, 0.105, 0.110, 0.115, 0.120, 0.125, 0.130, 0.135, 0.140, 0.145, 0.150, 0.155, 0.160, 0.165, 0.170, 0.175, 0.180, 0.185, 0.190, 0.195, to 0.25 mm; and wherein the length of the catheter ranges from 60, 70, 80, 90, 100, 110 to 120 cm and wherein the diameter of the guidewires ranges from about 0.01, 0.02, 0.03, 0.04, 0.05 to 0.06 mm. In one advantageous embodiment, the design conforms to a 5 Fr French catheter having an outer diameter of 1.67 mm, an inner diameter of 1.4 mm, and a wall thickness of 0.135 mm; see FIG. 10. Preferably, the guidewires are coated with a lubricant to facilitate pulling, pushing and other guidewire manipulations within the annular space.

In some embodiments, the total diameter of the catheter including the lumen and tubular layers ranges from 1.5, 2, 3, 4, 5, 6 to 7 Fr.

In other embodiments, the control shell comprises a rigid plastic material and is attached to, or near the proximal end of, the tubular section of the catheter. Usually or typically, the control shell comprises a wire holder or handle for each of the guidewires that is about 0.25, 0.5, 0.7 to 1.0 cm in diameter and the proximal ends of each guidewire comprise a tip that fits the wire holder or handle, preferably comprising a rigid plastic material. In some embodiments, the tubular portion of the catheter containing the lumen extends 5, 6, 7, to 8 cm past the control shell so as to permit access to the proximal end of the lumen.

The intermediate layer of the catheter may embed 1, 2, 3, 4, 5, 6, 7, 8, 9, 10 or more guidewires, preferably 6 to 8 wires evenly spaced around the circumference of the tubular layer segment.

The control shell containing the guidewire holders may have an oval or circular cross-section and comprises evenly spaced guidewire holder slots to accommodate each guidewire around its circumference and wherein the tips of each guidewire operably project from the wire holder slots. In some embodiments, the guidewires may comprise a low-friction coating or lubricant. In some embodiments, the bore or lumen of the catheter extends beyond the control shell to permit access to the lumen, for example, the proximal end of the lumen may be equipped with a cannula for injecting a drug or imaging material through the lumen into a target site.

Figure 7:
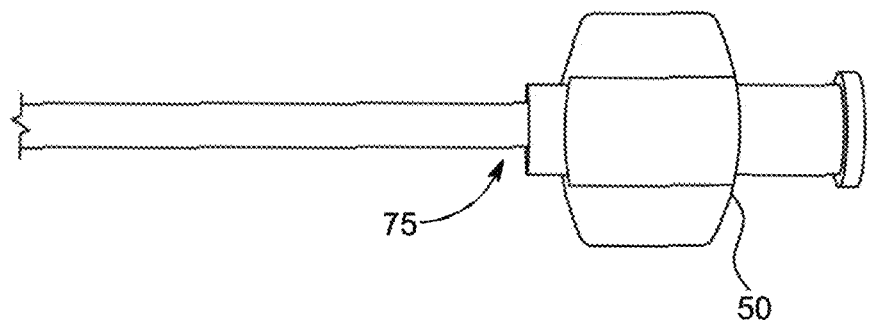
FIG. 7 describes a proximal end 75 of a catheter with a hub 50.

Typically, the control shell will be 5, 6, 7 to 8 cm from the proximal end of the catheter circling the external diameter of the catheter. Preferably, it does not affect the insertion of any mechanical devices or the injection of contrast agent through the lumen of the proximal end of the catheter. This proximity helps the operator to control the wires. The proximal end of the catheter may carry a hub as shown by FIG. 7 which has a central bore that tapers outwardly from the distal to the proximal end of the hub. This configuration is similar to most commercially available endovascular catheters. Any mechanical devices can be inserted into lumen of the catheter through this hub.

The outer layer and intermediate layer may comprise one or more medically acceptable polymers or polymer-containing compositions, preferably selected from the group consisting of silicone, polyether block polymers, polyamide, polyurethane, polyethylene or PTFE; and the exterior surface and/or the inner layer preferably comprise a low-friction or frictionless material such as PTFE. The support or mesh-like layer comprises, consists essentially of, or consists of a metal mesh, preferably a stainless steel wire mesh such as braided stainless steel mesh, which is divided into two parts by the V-shaped groove or void. In some alternative embodiments, the support or mesh-like layer may comprise a medically acceptable polymer such as those described above.

In some embodiments, the inner layer may be further coated or lubricated with a material that reduces friction. In some embodiments, the outer layer comprises a thermoplastic material containing nylon and/or polyurethane; the intermediate layer comprises nylon polyurethane; and/or the intermediate layer comprises nylon polyurethane and wherein the guidewires comprise flexible stainless steel.

In other embodiments, the circumferential V-shaped void forms an isosceles triangle that has its base adjacent to, or embedded in, the external layer and its base angles each range from 10, 15, 20, 25 to 30 degrees and the vertex angle ranges from 120, 130, 140, 150 to 160 degrees. The circumferential V-shaped void may form an isosceles triangle having an altitude ranging from 0.03, 0.04, 0.05, 0.06, 0.07 to 0.08 mm. In some embodiments the base of this triangle abuts or is slightly embedded in the external layer, but does not penetrate the external layer. The support or mesh-like layer can include a stainless steel wire mesh such as braided stainless steel mesh that is divided into two parts by the V-shaped groove or void.

The support layer comprises a material such as a mesh, grid, cables, or fibers that help give support and flexibility to the tubular segment of the catheter. In one embodiment, this layer comprises a cable or diamond cable patterned stainless steel mesh that is interrupted by the V-shaped defect and may comprise braided cable or diamond cable stainless steel mesh. In other embodiments, it may comprise a mesh comprising one or more synthetic polymers or nanofibers.

Another embodiment of the invention is directed to method for treating a patient having vascular disease or disorder comprising inserting and steering the catheter as disclosed herein by manipulating the guidewires using the control shell. A patient may be in need of endovascular surgery or angioplasty or treatment of vascular abnormality. The catheter may be used to place a stent or coils or introduce a contrast agent or dye to a particular anatomical location.

In some embodiments of this method the patient is in need of correction of a malformation in an artery or vein, or treatment of a nidus or other arteriovenous malformation, and the catheter is used to place an occlusion material or device to treat the malformation.

Another aspect of the invention is a method for making the steerable catheter as disclosed herein. Many of the fastening, connection, wiring, control, manufacturing and other means and components utilized in this invention are widely known and used in the field of the invention and their exact nature or type is not necessary for a person of ordinary skill in the art or science to understand the invention; therefore they will not be discussed in detail. Furthermore, the various components shown or described herein for any specific application of this invention can be varied or altered and anticipated by this invention and the practice of a specific application or embodiment of any element may already be widely known or used in the art, or persons skilled in the art or science; therefore, each will not be discussed in significant detail.

Manufacturing an endovascular catheter follows many of the steps used to produce conventional or non-steerable catheters. The basic steps include the following forming a tubular/cylindrical shaped structure for the catheter layers. These may be assembled by machine or manually. An annular/circular opening is formed in the intermediate layer to seat the wire threads/guidewires. Another cut is formed in the distal catheter to form a joint in the intermediate layer and the mesh-like layer before these layers are assembled with the external layer. The external layer and control shell are then added. A small opening in the external layer at the control shell attachment site is created allowing for the wire threads to pass from the intermediate layer and be held by the control shell. Lastly, wire threads are added through the intermediate layer opening and fused with distal end tip and threaded through the annular opening to the proximal end/control shell. These steps can be rearranged or modified depending on the exact type of manufacturing process selected or on user preferences.

In many embodiments, the intermediate layer contains 8 annular/rounded shaped holes in which 8 wires are threaded which extend from the wire tips (110) in the proximal end through the intermediate layer passing through the joint "defect" and reaching to the distal end of the catheter. The V-shaped defect or void may be produced according to the particular manufacturing process. For example, a cut may be applied through the intermediate layer, rather than producing the defect by assembly of two sections, and mesh-like layer before applying the external layer. In other embodiments, the defect may be produced by assembly a distal and proximal segment comprising the intermediate and mesh-like layers followed by application of the external layer.

Figure 8A:
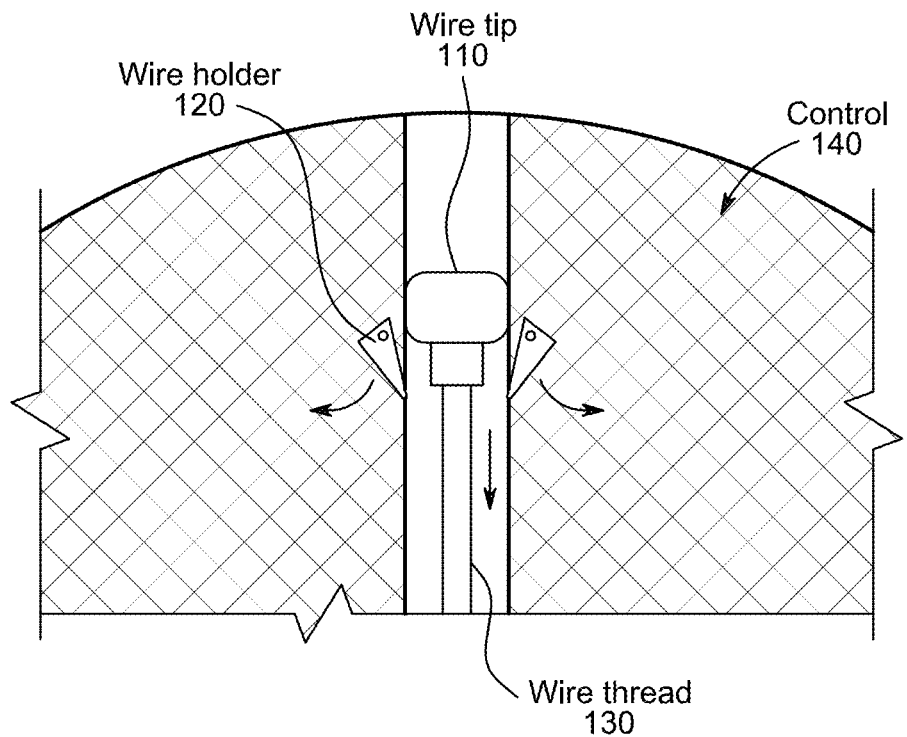
FIGS. 8A-8B detail the control shell 140 and shows pushing of one of the wire tips 110 and wire threads 130 inwards. This results in movement of an opposing wire thread in an opposite direction due to tension within the joint. Reference character 120 depicts the wire holder.
Figure 8B:
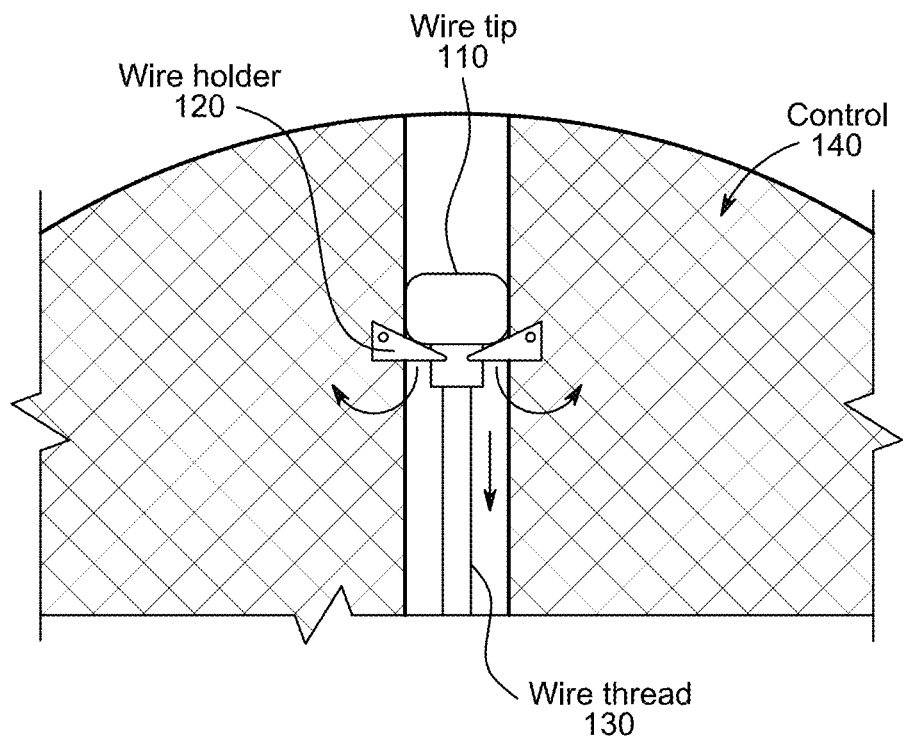
Figure 9:
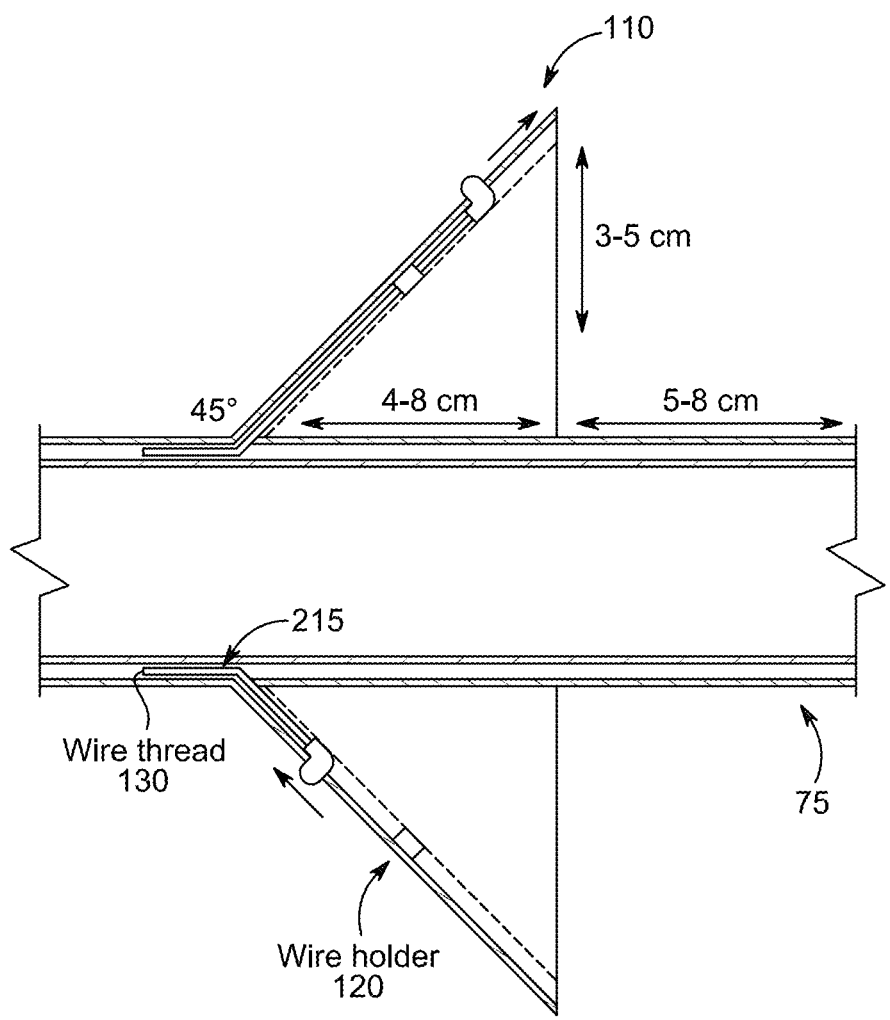
FIG. 9 shows a cross section of the control shell 140 and opposing wire tips 110 and wire threads 130. As the supper wire is pulled outwardly (proximally), the opposing wire tip and wire thread is pulled inwardly (distally) due to tension within the joint. Reference character 120 depicts the wire holder.

The 8 wires are typically equally distributed about midway within control shell by a wire tip holders (120). If an operator desires to direct the tip to one direction, he/she will pull the desired wire toward him and this will cause tension in the distal joint with changes in the tip direction; see FIGS. 8A, 8B and 9. When the operator pulls the desired wire, simultaneously the opposite wire will be pushed in opposite direction due to tension within the joint.

Terminology

Terminology used herein is for the purpose of describing particular embodiments only and is not intended to be limiting of the invention.

As used herein, the terms "axial" and "longitudinal" are used interchangeably and refer to a direction, orientation, or line that is parallel or substantially parallel to the central axis of the tubular section of the catheter or central axis of the control shell. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e. radial strength.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A steerable catheter, comprising: an external control shell, and tubular layers comprising in an order from external to internal, an outer layer, an intermediate layer, a support layer, and an inner layer that faces a lumen; wherein the intermediate layer comprises two to ten longitudinal guidewires embedded therein and spanning a length of the catheter; wherein the longitudinal guidewires each have distal and proximal ends and are longitudinally threaded through the intermediate layer and attached at each of the distal ends to a distal end of the catheter and attached at each of the proximal ends to the external control shell, wherein the longitudinal guidewires extend from a proximal end of the catheter and a distal end attachment is configured to be extendably or retractably moved along the length of the catheter and wherein the intermediate layer and the support layer comprise a circumferential V-shaped void which acts as a joint 1 to 5 cm from the distal end of the catheter with an apex of the V-shaped void facing towards the lumen and dividing the intermediate and support layers into unconnected distal and proximal intermediate and support layers, which V-shaped void does not divide the outer and inner layers and does not divide the two to ten longitudinal guidewires embedded in the intermediate layer; and wherein the inner layer surrounds the lumen.

2. The steerable catheter of claim 1, wherein a thickness of the outer layer ranges from 0.03 to 0.08 mm, a thickness of the intermediate layer ranges from 0.02 to 0.06 mm, a thickness of the support layer ranges from 0.012 to 0.02 mm; and a thickness of the inner layer range from 0.015 to 0.045 mm; wherein a total thickness of the tubular layers does not exceed 0.25 mm; and wherein the length of the catheter ranges from 60-120 cm and wherein a diameter of the longitudinal guidewires ranges from 0.01 to 0.06 mm.

3. The steerable catheter of claim 1, wherein a total diameter of the catheter is from 1.5 Fr to 7 Fr.

4. The steerable catheter of claim 1, wherein the external control shell is located about 5 to 8 cm from the proximal end of the catheter and comprises a rigid plastic material, wherein the external control shell comprises a handle for each of the longitudinal guidewires that is about 0.25 to 0.75 cm in diameter, and wherein each of the proximal ends of the longitudinal guidewires comprise a tip comprising a rigid plastic material.

5. The steerable catheter of claim 1, wherein a number of longitudinal guidewires in the intermediate layer is eight.

6. The steerable catheter of claim 1, wherein the external control shell has an oval or circular cross-section and comprises eight evenly spaced wire holder slots around a circumference thereof and wherein tips of each of the longitudinal guidewire operably project from the wire holder slots.

7. The steerable catheter of claim 1, wherein the outer layer and the intermediate layer, each comprise one or more medically acceptable polymers selected from a group consisting of a silicone, a polyether block polymer, a polyamide, a polyurethane, a polyethylene, and a polytetrafluoroethylene (PTFE);
wherein a mesh-like layer comprises a stainless steel wire mesh; and
wherein the inner layer comprises PTFE or a medically acceptable low friction polymer.

8. The steerable catheter of claim 1, wherein the outer layer comprises a nylon polyurethane material.

9. The steerable catheter of claim 1, wherein the intermediate layer comprises a nylon polyurethane material.

10. The steerable catheter of claim 1, wherein the intermediate layer comprises a nylon polyurethane material and wherein the longitudinal guidewires comprise stainless steel.

11. The steerable catheter of claim 1, wherein the circumferential V-shaped void forms an isosceles triangle that has a base adjacent to, or embedded in, the external layer and its base angles that range from 10 to 30 degrees and a vertex angle that ranges from 120 to 160 degrees.

12. The steerable catheter of claim 1, wherein the circumferential V-shaped void forms an isosceles triangle having an altitude ranging from 0.03 to 0.08 mm.

13. The steerable catheter of claim 1, wherein the support layer comprises a stainless steel wire mesh that is divided into two parts by the circumferential V-shaped void.

14. The steerable catheter of claim 1, wherein the support layer comprises a cable or diamond cable patterned stainless steel mesh that is interrupted by the circumferential V-shaped void.

15. The steerable catheter of claim 1, wherein the support layer comprises a braided, cable or diamond cable stainless steel mesh.

16. A method for treating a patient having vascular disease or disorder comprising inserting and steering the steerable catheter of claim 1 by manipulating the longitudinal guidewires using the external control shell.

17. The method of claim 16, comprising endovascular surgery.

18. The method of claim 16, comprising angioplasty or treatment of vascular abnormality and the steerable catheter is used to place a stent or coils.

19. The method of claim 16, comprising treatment of a nidus or other arteriovenous malformation, and the steerable catheter is used to place an occlusion material or device to treat the arteriovenous malformation.

20. The method of claim 16, comprising endovascular administration of medication and the steerable catheter is used to administer the medication.

* * * * *